United States Patent [19]
Beyerle et al.

[11] Patent Number: 5,976,578
[45] Date of Patent: Nov. 2, 1999

[54] LIQUID ANTACID COMPOSITIONS

[75] Inventors: Douglas S. Beyerle, Horsham; John Case, Doylestown; Gerard P. McNally, Strafford; Frank Hatch, Doylestown, all of Pa.

[73] Assignee: McNeil-PPC, Inc., Skillman, N.J.

[21] Appl. No.: 08/932,625

[22] Filed: Sep. 17, 1997

Related U.S. Application Data

[63] Continuation-in-part of application No. 08/728,590, Oct. 10, 1996, abandoned.

[51] Int. Cl.⁶ .......................... A61K 33/10; A61K 33/08
[52] U.S. Cl. ....................... 424/686; 424/687; 424/689; 424/690; 514/819
[58] Field of Search ........................... 514/819; 424/686, 424/687, 689, 690

[56] References Cited

U.S. PATENT DOCUMENTS

| | | |
|---|---|---|
| 4,585,790 | 4/1986 | Padfield et al. . |
| 4,861,592 | 8/1989 | Gottwald et al. . |
| 5,068,249 | 11/1991 | Long . |
| 5,431,916 | 7/1995 | White ........................................ 424/451 |
| 5,455,050 | 10/1995 | Beyerle et al. . |
| 5,498,426 | 3/1996 | Wilson et al. . |

FOREIGN PATENT DOCUMENTS

| | | |
|---|---|---|
| EP 0 138 540 | 4/1985 | European Pat. Off. . |
| EP 0 286 781 | 10/1988 | European Pat. Off. . |
| WO 9425008 | 11/1994 | European Pat. Off. . |
| WO 95/10274 | 4/1995 | WIPO . |

*Primary Examiner*—Raymond Henley, III
*Attorney, Agent, or Firm*—Kenneth J. Dow

[57] ABSTRACT

Liquid antacid compositions containing a tri- or di-ester buffer have a reduced final product pH providing for a more efficacious preservative system and better tasting product without compromising to acid neutralization capacity of the antacid.

19 Claims, No Drawings

LIQUID ANTACID COMPOSITIONS

CROSS REFERENCE TO RELATED APPLICATION

This application is a continuation-in-part of application Ser. No. 08/728,590, filed Oct. 10, 1996, now abandoned.

BACKGROUND OF THE INVENTION

1. Field of the Invention

The present invention relates to liquid antacid compositions and methods for their preparation. More particularly, the present invention relates to liquid antacid compositions containing a tri- or di-ester as a buffer. The compositions have a reduced final product pH providing for a more efficacious preservative system and better tasting product without compromising the acid neutralizing capacity of the antacid.

2. Description of the Related Art

Gastric antacids are agents that neutralize or remove acid from the gastric contents. Antacids are widely used in the treatment of various gastrointestinal disorders such as peptic ulcers and gastritis. Antacids are also used for the relief of acid indigestion, heartburn, dyspepsia, sour stomach, reflux esophagitis and the like. The clinical use of antacids is based on their ability to neutralize stomach acid and increase the pH of gastric secretions. Although antacids do not neutralize all gastric acid, increasing gastric pH from 1.3 to 2.3 neutralizes 90% and increasing pH to 3.3 neutralizes 99% of gastric acid. For optimal healing of peptic ulcers, most clinicians believe that gastric pH should be maintained at about 3–3.5. Accordingly, it is desirable that an antacid feature a high acid neutralization capacity and a rapid rate of gastric acid neutralization.

Antacids used today are made from a variety of inorganic salts such as calcium carbonate, sodium bicarbonate, magnesium salts and aluminum salts. Magnesium hydroxide and aluminum hydroxide are the most potent magnesium and aluminum salts and are often used in combination. In addition, magnesium oxide, magnesium carbonate, aluminum phosphate, magaldrate, magnesium trisilicate, and aluminum sucrose sulfate (sucralfate) are also employed.

Antacids are available in both liquid suspensions as well as solid dosage forms. In general, liquid antacid suspensions are preferred to tablets or powders since they are more rapidly and effectively solubilized and have a greater ability to react with and neutralize gastric acid.

One of the major concerns with formulating an antacid liquid is the preservative efficacy. Liquid antacid preparations are generally susceptible to microbial contamination. The pH of any aqueous based solution is critical to controlling the microbial growth within the solution. Generally, acidic solutions (pH 3–6) are less susceptible to microbial growth than alkaline solutions (pH 8–9). Under most circumstances, the ability to restrict this microbial growth can be aided by the addition of a preservative. The degradation of the preservative in solution can in turn be affected by the pH of the finished product. In most situations, there is a perfect match between the finished product's pH and the pH range at which the preservative is most efficacious.

Some liquid antacid preparations, for example calcium carbonate, however, generally have a pH above 8.0 and no preservative systems approved in the United States function optimally at this pH. The alkyl esters of para-hydroxybenzoic acid (the parabens, e.g. butylparaben, methylparaben and propylparaben) are most widely used as preservatives because they offer the most efficacious option, but they degrade over time and this degradation process increases exponentially with an increase in pH. Consequently, in order to achieve adequate preservative levels throughout the shelf life of the product, higher levels of the preservative must be added initially. This can affect the taste of the finished product however, because preservatives such as the parabens are known to have a poor taste.

Accordingly, there is a need for a preservative system for highly alkaline liquid antacid preparations which effectively inhibits microbial contamination over the shelf life of the product without adversely affecting the taste of the finished product.

One way to inhibit degradation of the preservative would be to lower the pH of the antacid suspension. This may be done through the addition of buffers such as citric acid and tartaric acid. For example, U.S. Pat. No. 5,455,050 discloses calcium carbonate/magnesium salt antacid suspensions containing a carboxylic acid buffering agent such as tartaric acid. However, in order to lower the pH sufficiently to a level of around pH 7 where preservative degradation is minimal, large amounts of these buffers are required. The addition of such amounts of these acidic buffers can in turn adversely affect the acid neutralizing capacity of the antacid. Thus, there is a need for a method of reducing the pH of the antacid suspension to inhibit degradation of the preservative without adversely affecting the acid neutralizing capacity of the liquid antacid preparation.

Patent Application EP 0138540 describes liquid cimetidine suspensions which may contain an antacid, where the suspensions contain a buffer to maintain the pH at greater than 7 to enhance the taste of the suspension. Cimetidine has a pronounced bitter taste. The pH is preferably 7.2–7.8 and the buffer is preferably sodium citrate.

SUMMARY OF THE INVENTION

The invention relates to liquid antacid preparations having enhanced preservative efficacy comprising one or more acid neutralizing compounds in combination with a preservative and a tri- or di-ester buffer to maintain the pH at less than 8.0. Superior preservative efficacy is achieved because preservative degradation is minimized by maintaining the pH below 8.0. Improved taste is also possible because less preservative is necessary as a result of the reduced degradation. The use of the tri- or di-ester buffer allows the pH of the preparation to be lowered without compromising the acid neutralizing capacity of the antacid.

In another aspect of the invention, a histamine H2 receptor antagonist may be added to the antacid preparation. An added benefit is thus realized as the pH of less than 8.0 is optimal for the stability and taste masking of the histamine H2 receptor antagonist.

DETAILED DESCRIPTION

The invention relates in particular to liquid antacid preparations comprising an effective amount of an acid neutralizing compound, a preservative and a tri- or di-ester compound such as triacetin as a buffer to maintain the pH of the liquid preparation below 8.0 and optionally, one or more other pharmaceutically acceptable additives. Preferably, the preparation contains 200 mg–2000 mg/5 ml acid neutralizing compound, 1 mg–5 mg/5 ml preservative and 2 mg–100 mg/5 ml tri- or di-ester buffer.

The antacid compounds are applicable for use as the active acid neutralizing compound in the present invention are those which are highly alkaline in aqueous solution having a pH greater than 8.0 and which are capable of being buffered by triacetin to a pH below 8.0. Calcium carbonate in the range of 200 to 2000 mg per 5 ml is preferred, but magnesium carbonate, magnesium trisilicate, aluminum hydroxide and magnesium hydroxide and mixtures thereof may also be employed. The amount of antacid in the preparation may conveniently be, for example, in the range of 5% to 35% w/v of the composition. A mixture containing from about 5 to about 15% w/v calcium carbonate and about 2 to about 8% magnesium carbonate or magnesium trisilicate may advantageously be employed. The active acid neutralizing compounds are generally utilized as individual powders, preferably micronized powders.

The preservative component may be selected from any pharmaceutically acceptable preservative. The alkyl esters of para-hydroxybenzoic acid (the parabens, e.g. butylparaben, methylparaben and propylparaben) are preferred and may be used alone or in combination. Generally, the parabens are used in a concentration of about 0.02% w/v. Other preservatives include ethylenediamine tetra-acetic acid, propyl-p-hydroxybenzoates or sorbic acid.

The tri- or di-ester buffer is an organic buffer having two or three ester functionalities of the formula R'COOR such as triacetin (glyceryl triacetate), a triester of glycerin and acetic acid which is commonly used as a pharmaceutical additive for a variety of uses. Other tri- and di-ester buffers useful in the present invention are exemplified by triethyl citrate, acetyltriethyl citrate, acetyltri-n-butyl citrate and diacetin (1,2,3-propanetriol diacetate). The tri- or di-ester buffer is added in an amount to bring the pH of the preparation to a level below 8.0. For example, the tri- or di-ester buffer may constitute 0.04 to 2% w/v of the composition, generally in the range of 5–25 mg/5 ml. The pH of the final product is below 8.0, preferably in the range of 6–7.5. The preferred buffers are triacetin, triethyl citrate and diacetin, most preferably triacetin.

Advantageously, the liquid antacid preparation may also contain a histamine H2 receptor antagonist. Histamine H2 receptor antagonists are agents which reduce acid secretion and are effective in the treatment of many gastric disorders. Co-administration of histamine H2 receptor antagonists and an antacid is known for example from U.S. Pat. No. 5,229,137 and WO 92/00102. Any of the known histamine H2 receptor antagonists may be used such as cimetidine, ranitidine, nizatidine and famotidine.

Through application of the present invention, an added benefit is realized when the histamine H2 receptor antagonist is added in that the histamine H2 receptor antagonists exhibit enhanced stability and palatability in aqueous solutions having the pH levels of the compositions of the present invention. For example, it is known from U.S. Pat. No. 4,585,790 that ranitidine aqueous based formulations show enhanced stability in the pH range of 6.5–7.5. Similarly, European Patent Application EP 138540 discloses the fact that cimetidine oral aqueous based formulations have improved flavor in the pH range of 7.2–7.8. Thus, the use of the present invention, which allows the pH of the liquid antacid preparation to be maintained below 8.0 without compromising the acid neutralizing capacity of the antacid, is of added benefit when used in conjunction with a histamine H2 receptor antagonist because it imparts added stability and palatability to the preparation. A typical preparation will contain about 100 mg to about 400 mg of cimetidine, or 50 mg to about 150 mg of ranitidine or 10 mg to 40 mg of famotidine per dosage unit (e.g., per 5 ml). Typically, the histamine H2 receptor antagonist is employed as the free base or, in the form of the physiologically acceptable salt, such as the hydrochloride salt in the case of ranitidine.

The composition according to the invention, in unit dosage form, may be administered, for example 1 to 4 times per day. The dosage will depend on the active agents that are employed, the condition being treated and the age and weight of the patient. Typical dosages include about 5–30 mls of the preparation containing the dose of antacid selected to achieve the desired acid neutralizing effect. A suitable dose range for calcium carbonate is 200 mg to 2.0 g.

The liquid compositions of the invention are aqueous suspensions containing the active ingredients in admixture with pharmaceutically acceptable excipients typically found in aqueous suspensions for oral administration. Such excipients may be suitable suspending agents, for example, sodium alginate, polyvinylpyrrolidone, gum tragacanth, gum acacia, xanthan gum, locust bean gum and cellulose derivatives such as sodium carboxymethylcellulose, microcrystalline cellulose, hydroxy ethylcellulose, methyl cellulose or hydroxypropyl methylcellulose or mixtures thereof. Also included may be dispersing or wetting agents such as sorbitan esters or lecithin, antigelling additives, surface modifiers, aqueous or non-aqueous vehicles such as sorbitol solution, ethyl alcohol or fractionated vegetable oils, or diluents.

The compositions may also contain flavorings, colorants and/or sweeteners as appropriate. Suitable flavorants include fruit flavors, peppermint, licorice or bubble gum flavors. The sweetening agents may be for example bulk sweeteners such as sugars (e.g. sucrose or fructose) or polyols (e.g. maltitol, sorbitol) and/or intense sweeteners such as saccharin, aspartame or acesulfame K.

In addition to the tri or di-eseter buffer such as triacetin, the compositions may also contain other buffers and buffer salts such as tartaric acid or citric acid.

Other active agents may be added to the preparation. For instance, antiflatulents, analgesics, antidiarrheals, antispasmodic agents or anti-foaming agents like simethicone may be added as well as other gastrointestinal agents in dosage amounts conventionally used in the treatment of gastrointestinal dysfunction.

The liquid antacid compositions of the present invention may be prepared according to conventional techniques well known in the pharmaceutical industry. Thus, for example, the antacid, the preservative and the triacetin may be admixed, if desired, with suitable excipients and dispersed in the aqueous vehicle.

As stated, the use of a tri- or di-ester buffer to lower the pH of the antacid composition of the present invention provides for superior preservative efficacy because preservative degradation is minimized due to the lower pH. The use of the tri- or di-etser compound such as triacetin as the buffer allows one to do this without compromising the acid neutralizing capacity of the antacid. Additionally, since degradation of the preservative is inhibited, the level of the preservative can be reduced thereby improving the taste of the finished product. Alternatively, if the amount of preservative is not reduced, the expected shelf life of the product may be increased.

In order to further illustrate the present invention and the advantages thereof, the following specific examples are given, it being understood that these examples are intended only to be illustrations without serving as a limitation on the scope of the present invention.

EXAMPLE 1

Liquid Antacid Composition Containing Triacetin

A liquid antacid composition of the present invention was prepared containing the following ingredients:

| Ingredient | mg per 5 ml | gms/100 ml |
| --- | --- | --- |
| Calcium Carbonate, USP | 400 | 8.0 |
| Purified Water, USP | 3975 | 79.5 |
| Simethicone Emulsion, 30% USP | 6.6 | 0.13 |
| Sorbitol Solution, USP | 1000.0 | 20 |
| Xanthan Gum, NF | 16.25 | 0.325 |
| Microcrystalline Cellulose & Sodium Carboxymethylcellulose | 5.0 | 0.1 |
| Butylparaben, NF | 1.00 | 0.02 |
| Propylparaben, NF | 1.50 | 0.03 |
| Flavor | 25.0 | 0.50 |
| Sodium Saccharin | 1.425 | 0.0285 |
| Colorant | 0.055 | 0.0011 |
| Triacetin, USP | 5.0 | 0.10 |

In a suitable preparation vessel such as a clean stainless steel vessel, the sorbitol and water are added. The microcrystalline cellulose, sodium carboxymethylcellulose and simethicone are then added. The calcium carbonate is then added and mixed for fifteen minutes. The xanthan gum is then added and mixed for thirty minutes. In a separate vessel, the flavor, parabens, red shade, and triacetin are mixed until the parabens have dissolved.

The contents from the separate vessel are then added to the preparation vessel and mixed for thirty minutes. The suspension is then homogenized at 500 psi. and pasteurized at 68° C. and filled into bottles.

pH Buffering

The pH of the composition of Example 1, containing 5 mg/5 ml triacetin, Example 1a containing 25 mg/5 ml triacetin and Example 1b containing 25 mg/5 ml triacetin with 25 mg/5 ml tartaric acid, were tested over time and compared with control compositions containing no buffer and comparative compositions containing 25 mg/5 ml tartaric acid. The results are set forth in Table 1.

TABLE 1

| Ex # | Init. | 10 Days | 2 Wks | 3 Wks | 4 Wks | 5 Wks | 6 Wks | 7 Wks |
| --- | --- | --- | --- | --- | --- | --- | --- | --- |
| Cont. | 8.9 | | | | | | | |
| Comp. E | 8.11 | 8.11 | 8.02 | 7.95 | 7.86 | 7.85 | | |
| Ex 1a | 7.8 | 7.69 | 7.63 | 7.52 | 7.32 | 7.21 | 7.17 | 7.15 |
| Ex 1b | 7.7 | 7.09 | 7.05 | 6.98 | 6.6 | 6.6 | 6.62 | 6.62 |
| Ex 1c | 7.36 | 6.85 | 6.83 | 6.75 | 6.71 | | | |

Control (No Buffer)
Comparative Example (artaric Acid 25 mg/5 ml)
Example 1a (Triacetin 5 mg/5 ml)
Example 1b (Triacetin 25 mg/5 ml)
Example 1c (Tartaric Acid 25 mg/5 ml + Triacetin 25 mg/5 ml)

The foregoing table demonstrates that triacetin was effective in maintaining the pH of the antacid composition below 8.0 over the period of time measured.

Acid Neutralizing Capacity

The acid neutralizing capacity (ANC) of the antacid composition was also measured for the composition of Examples 1 and 2 at the 4 week interval. The results demonstrated that the ANC was 7.99 mEq/5 ml. The theoretical ANC for the antacid composition was 8 mEq/ 5 ml. Accordingly, the results showed that there was minimal effect of the triacetin buffer on the ANC of the antacid composition.

Preservative Degradation

The degradation of propyl and butyl paraben preservatives in the aqueous antacid suspension of the present invention was measured and compared with aqueous antacid suspensions without buffer and compositions containing 25 mg/5 ml tartaric acid. The results are set forth in Table 2.

TABLE 2

PARABEN STUDY

| | INITIAL LEVELS | | | |
| --- | --- | --- | --- | --- |
| | propyl % w/v | butyl % w/v | pH | ANC |
| Comp. 1 | 96.3 | 98.1 | 8.32 | 8 |
| Comp. 2 | 97.6 | 97.7 | 7.7 | 7.8 |
| Example 1 | 99.8 | 95.6 | 7.95 | 7.8 |
| Example 2 | 97 | 98.9 | 7.44 | 8 |

ONE MONTH @ 40° C.

| | propyl % | butyl % | pH |
| --- | --- | --- | --- |
| Comp. 1 | 78.5 | 77.3 | 8.4 |
| Comp. 2 | 87.1 | 83.3 | 7.7 |
| Example 1 | 93.9 | 92 | 7.45 |
| Example 2 | 95.9 | 92 | 6.98 |

Comp. 1-(Comparative Example 1)-1.75 mg Tartaric Acid
Comp. 2-(Comparative Example 2)-25 mg Tartaric Acid
Example 1-5 mg Triacetin
Example 2-25 mg Triacetin The foregoing results set forth in Table 2 demonstrate that the antacid suspensions of the present invention show decreased degradation of the preservative at one month than the compositions containing the tartaric acid buffer.

EXAMPLE 2

FORMULATION CONTAINING CALCIUM CARBONATE AND RANITIDINE

| | mg/5 ml |
| --- | --- |
| Rantidine.HCl (equiv. to 75 mg. rantidine) | 83.000 |
| CaCO₃ powder | 400.000 |
| Simethicone (30% Emulsion) | 6.600 |
| Sorbitol (70% soln.) | 1000.000 |
| Xanthan Gum | 16.2 |
| D.I. Water | 3900.000 |
| Triacetin, USP | 25.000 |
| Flavor | 25.000 |
| Sodium Saccharin | 1.425 |
| Propylparaben NF | 1.500 |
| Butylparaben NF | 1.500 |
| | 5383.275 |

Place 500.0 g. of deionized water and 200 g. of 70% sorbitol solution in a 1.5 liter vessel equipped with a IKA mixer. With the agitator set at high speed add the CaCO₃ powder. When the CaCO₃ has been completely dispersed add 3.25 g. of xanthan gum to the mixture. Continue mixing until all of gum has dissolved. Next add the 1.32 g. of simethicone emulsion to the vessel also under high speed agitation. Once the simethicone emulsion has been completely dispersed add the following ingredients in sequence; 168 g. of ranitidine.HCl, 0.3 g. butylparaben, 0.3 g. propylparaben, 5.0 g. flavor, 0.285 g of sodium saccharin, 5.0 g of triacetin, finally add 280 g. of deionized water.

The suspension was then homogenized and pasteurized into plastic bottles.

EXAMPLE 3

Liquid Antacid Composition Containing Diacetin

A liquid antacid composition of the present invention is prepared in accordance with Example 1 substituting 25 mg/5 ml Diacetin for the Triacetin used in Example 1.

EXAMPLE 4

Liquid Antacid Composition Containing Triethyl Citrate

A liquid antacid composition of the present invention is prepared in accordance with Example 1 substituting 25 mg/5 ml Triethyl Citrate for the Triacetin used in Example 1.

pH Buffering

The pH of the composition of Examples 3 and 4, containing 25 mg/5 ml Diacetin and 25 mg/5 ml Triethyl Citrate, were tested over time and compared with control compositions containing no buffer. The results are set forth in Table 3.

TABLE 3

| Buffer | Initial pH | 1 month pH | 2 month pH |
|---|---|---|---|
| Control** | 9.1 | 9.1 | 9.1 |
| Triacetin | 8.0 | 6.8 | 6.8 |
| Diacetin | 7.9 | 6.9 | 6.8 |
| Triethyl Citrate | 8.0 | 7.0 | 6.9 |

**The control consisted of 8 g of calcium carbonate (400 mg/5 ml) and 92 g purified water. A similar base was used for the other three batches.

The data set forth in Table 3 shows that the pH of the mixtures containing Diacetin and triethyl citrate were effective in maintaining the pH of the antacid composition below 8.0 over the period of time measured, similar to the triacetin of Example 1.

We claim:

1. A liquid antacid preparation comprising an effective amount of one or more acid neutralizing compounds, a preservative, 0.04 to 2% w/v of a tri- or di-ester buffer and optionally, one or more other pharmaceutically acceptable additives, in an aqueous vehicle wherein the pH of the liquid preparation is below 8.0.

2. A liquid antacid preparation according to claim 1, comprising 200 mg–2000 mg/5 ml acid neutralizing compound, 1 mg–5 mg/5 ml preservative and 2 mg–100 mg/5 ml tri- or diester buffer.

3. A liquid antacid preparation according to claim 1, wherein the pH of the final product is in the range of 6–7.5.

4. A liquid antacid preparation according to claim 1 wherein the acid neutralizing compound is calcium carbonate.

5. A liquid antacid preparation according to claim 1 wherein the acid neutralizing compound is selected from calcium carbonate, magnesium carbonate and magnesium trisilicate and mixtures thereof.

6. A liquid antacid preparation according to claim 1 wherein the preservative is selected from the alkyl esters of para-hydroxybenzoic acid (the parabens).

7. A liquid antacid preparation according to claim 6 wherein the preservative is selected from butylparaben, methylparaben and propylparaben.

8. A liquid antacid preparation according to claim 1, containing 5–25 mg/5 ml triacetin.

9. A liquid antacid preparation according to claim 1, containing 5–25 mg/5 ml diacetin.

10. A liquid antacid preparation according to claim 1, containing 5–25 mg/5 ml triethyl citrate.

11. A liquid antacid preparation according to claim 1, further containing a pharmaceutically effective amount of a histamine H2 receptor antagonist.

12. A liquid antacid preparation according to claim 11, wherein the histamine H2 receptor antagonist is selected from cimetidine, ranitidine, nizatidine and famotidine.

13. A liquid antacid preparation according to claim 12, containing 100 mg to about 400 mg of cimetidine per dose.

14. A liquid antacid preparation according to claim 12, containing 50 mg to about 150 mg of ranitidine per dose.

15. A liquid antacid preparation according to claim 12, containing 5 mg to 40 mg of famotidine per 5 ml.

16. A method for the treatment of a gastrointestinal disorder in a human in which acid neutralization is desired which comprises administering to said human an effective amount of a liquid antacid composition of claim 1.

17. A method for the treatment of a gastrointestinal disorder in a human in which acid neutralization is desired which comprises administering to said human an effective amount of a liquid antacid composition of claim 11.

18. A method according to claim 16 wherein the gastrointestinal disorder is selected from the group consisting of acid indigestion, heartburn, dyspepsia, sour stomach, and reflux esophagitis.

19. A method of enhancing the effectiveness of a preservative in a liquid antacid composition by maintaining the pH of the composition below 8.0 through the addition of a tri- or di-ester buffer.

* * * * *